(12) United States Patent
Talmadge et al.

(10) Patent No.: US 6,649,189 B2
(45) Date of Patent: Nov. 18, 2003

(54) METHODS FOR USE OF DELIVERY COMPOSITION FOR EXPANDING, ACTIVATING, COMMITTING OR MOBILIZING ONE OR MORE PLURIPOTENT, SELF-RENEWING AND COMMITTED STEM CELLS

(75) Inventors: James E. Talmadge, Bellevue, NE (US); Gary J. Rosenthal, Louisville, CO (US); Jeffrey B. Etter, Boulder, CO (US)

(73) Assignee: RxKinetix, Inc., Louisville, CO (US)

( * ) Notice: Subject to any disclaimer, the term of this patent is extended or adjusted under 35 U.S.C. 154(b) by 32 days.

(21) Appl. No.: 09/893,372

(22) Filed: Jun. 26, 2001

(65) Prior Publication Data

US 2002/0028515 A1 Mar. 7, 2002

Related U.S. Application Data

(60) Provisional application No. 60/214,298, filed on Jun. 26, 2000, and provisional application No. 60/274,891, filed on Mar. 9, 2001.

(51) Int. Cl.⁷ .................................. A61K 9/14
(52) U.S. Cl. ........................... 424/486; 514/2; 424/482; 424/468; 424/93.1; 525/420
(58) Field of Search .............................. 514/2; 424/486, 424/468, 482, 93.1; 525/420

(56) References Cited

U.S. PATENT DOCUMENTS

| | | | |
|---|---|---|---|
| 5,702,717 A | 12/1997 | Cha et al. .................... 424/425 |
| 5,728,581 A | 3/1998 | Schwartz et al. ............. 435/385 |
| 5,851,984 A * | 12/1998 | Matthews ........................ 514/2 |
| 5,861,174 A | 1/1999 | Stratton et al. .............. 424/484 |
| 5,902,110 A | 5/1999 | Alfano et al. ................ 433/215 |
| 5,980,912 A | 11/1999 | Podolski et al. .......... 424/278.1 |
| 6,004,573 A * | 12/1999 | Rathi .......................... 424/426 |
| 6,017,527 A | 1/2000 | Maraskovsky et al. .. 424/93.71 |
| 6,043,389 A | 3/2000 | Nudelman et al. ............ 560/55 |
| 6,054,315 A * | 4/2000 | Cummings .................. 435/375 |
| 6,218,148 B1 | 4/2001 | Zsebo et al. ............... 435/69.5 |
| 6,451,346 B1 * | 9/2002 | Shah .......................... 424/486 |
| 2002/0156034 A1 * | 10/2002 | Tudan .......................... 514/44 |

FOREIGN PATENT DOCUMENTS

| | | | |
|---|---|---|---|
| WO | WO 98/02142 | * | 1/1998 |
| WO | WO 99/32135 | | 7/1999 |
| WO | WO 99/36107 | | 7/1999 |
| WO | WO 99/65521 | | 12/1999 |
| WO | WO 00/33764 | | 6/2000 |
| WO | WO 00/56361 | | 9/2000 |
| WO | WO 00/56362 | | 9/2000 |
| WO | WO 01/12218 A1 | | 2/2001 |

\* cited by examiner

*Primary Examiner*—Dave T. Nguyen
(74) *Attorney, Agent, or Firm*—Marsh Fischmann & Breyfogle LLP

(57) ABSTRACT

A hematopoietic growth factor delivery composition includes a hematopoietic growth factor, a liquid vehicle, a first biocompatible polymer and a second biocompatible polymer. The composition exhibits reverse-thermal viscosity behavior, due to interaction between the first biocompatible polymer and the liquid vehicle. The second biocompatible polymer helps to protect the first biocompatible polymer from being dissolved in vivo following administration to a host.

79 Claims, 5 Drawing Sheets

METHODS FOR USE OF DELIVERY COMPOSITION FOR EXPANDING, ACTIVATING, COMMITTING OR MOBILIZING ONE OR MORE PLURIPOTENT, SELF-RENEWING AND COMMITTED STEM CELLS

CROSS-REFERENCE TO RELATED APPLICATIONS

This application claims a priority benefit under 35 U.S.C. §119(e) to U.S. Provisional Patent Application No. 60/214,298 entitled "COMPOSITION AND METHOD FOR DELIVERY OF HEMATOPOIETIC GROWTH FACTOR" filed Jun. 26, 2000 and to U.S. Provisional Patent Application No. 60/274,891 entitled "COMPOSITION AND METHOD FOR DELIVERY OF HEMATOPOIETIC GROWTH FACTOR" filed Mar. 9, 2001, the entire contents of each of which are incorporated herein by reference as if each were set forth herein in full.

FIELD OF THE INVENTION

The present invention relates to methods for expanding, activating, committing or mobilizing pluripotent self-renewing and committed stem cells.

BACKGROUND OF THE INVENTION

Functionally, hematopoietic growth factors can be considered to belong to one of three groups. The first or multilineage group includes interleukin 3 (IL-3) and granulocyte macrophage colony stimulating factor (GM-CSF) which act on early colony forming units (CFU's) including colony forming unit-granulocyte, erythrocyte, megakaryocyte, macrophage (CFU-GEMM), colony forming unit-granulocyte-macrophage (CFU-GM), burst forming units erythrocyte (BFU-E) or megakaryocytes, (BFU-MK). The second or unilineage group includes erythropoietin (EPO), granulocyte colony stimulating factor (G-CSF), interleukin 5 (IL-5), macrophage colony stimulating factor (M-CSF) and thrombopoietin (TPO), and act on later hematopoietic progenitors (i.e., colony forming unit erythrocyte (CFU-E), colony forming unit megakaryocyte (CFU-Mk), and colony forming unit eosinophil (CFU-Eo). The third or "potentiating" group includes interleukin 6 (IL-6), interleukin 11 (IL-11), lymphocyte inhibitory factor (LIF), fibroblast growth factor basic (FGFb), stem cell factor (SCF) and Flt3 ligand (Flt3-L), and act to potentiate the activities of other hematopoietic factors. Within the third group, SCF and Flt3-L both show marked activity on hematopoietic stem cells and thus have been considered special circumstance/stem cell growth factors.

G-CSF and GM-CSF are two commonly used hematopoietic growth factors. The principal action of G-CSF is the stimulation of colony forming unit granulocyte (CFU-G), which in vivo manifests into an augmented production of polymorphonuclear leukocyte (neutrophil) as well as enhancing the phagocytic and cytotoxic functions of neutrophils in general. G-CSF has been shown to be effective in the treatment of severe neutropenia following autologous bone marrow transplantation and high-dose chemotherapy. GM-CSF and G-CSF are each used to decrease the period of neutropenia seen during this type of therapy and thereby reduces morbidity secondary to bacterial and fungal infections. When used as a part of an intensive chemotherapy regimen, G-CSF can decrease the frequency of both hospitalization for febrile neutropenia and interruptions in life-saving chemotherapy protocols. G-CSF also has proven to be effective in the treatment of severe congenital neutropenias. In patients with cyclic neutropenia, G-CSF therapy, while not eliminating the neutropenic cycle, will increase the level of neutrophils and shorten the length of the cycle sufficiently to prevent recurrent infections. G-CSF therapy can improve neutrophil counts in some patients with myelodysplasia or marrow damage. The neutropenia of AIDS patients receiving AZT also can be partially or completely reversed.

G-CSF is typically administered by subcutaneous injection or intravenous infusion at a dose of 1 to 20 $\mu$g/kg per day. The distribution and clearance rate from plasma (half-life of 3.5 hours) are similar for both routes of administration. A continuous, 24-hour intravenous infusion can be used to produce a steady-state serum concentration of the growth factor. As with GM-CSF therapy, G-CSF is given daily following bone marrow transplantation or intensive chemotherapy will increase granulocyte production and shorten the period of severe neutropenia. In bone marrow transplantation and intensive chemotherapy patients, continuous daily administration for 14 to 21 days or longer may be necessary to correct the neutropenia. With less intensive chemotherapy, fewer than 7 days of treatment may be needed.

Both G-CSF and GM-CSF will increase the number of marrow progenitor cells in the circulation, a particularly valuable function in patients preparing for stem cell collection. Post-transplant infusions of harvested stem cells together with G-CSF or GM-CSF may reduce the severity of the post-transplant neutropenia.

One hematopaetic growth factor that has recently received considerable attention for its unique properties is Flt3-L. Flt3-L is a transmembrane glycoprotein of approximately 30 kDa. Mouse and human Flt3-L share significant homology at the amino acid level (~70%), and show cross-species reactivity, so testing human Flt3-L in mouse produces the same or similar biological effects as would occur in the human. Cells known to express Flt3-L include human and mouse T cell lines, as well as architectural cells of the bone marrow, specifically the bone marrow fibroblast.

Some of the myelopoietic, or white blood cell potentiating effects attributed to Flt3-L include: I) an expansion of CD34+ CD38– cell number when used in conjunction with SCF and IL-3; 2) an increase in high proliferative potential colony forming cells (HPP-CFC) and CFU-GM numbers; and 3) in the presence of GM-CSF, the formation of large numbers of CFU-GM. Individual and direct myelopoietic effects of Flt3-L include an increase in CFU-GM, CFU-GEMM and HPP-CFC survival and a preferential induction of macrophages under certain conditions. Flt3-L alone apparently has minimal or no effects on erythroid and megakaryocyte progenitors.

There is substantial data showing that the system of Flt3-L and its receptor also plays an important role in lymphopoiesis, the processes involved in normal growth and maturation of lymphocytes. This important activity has been confirmed in mice made deficient for Flt3-L System. In these mice hematopoietic populations are essentially normal but marked deficiencies of early B cell progenitors are found in the bone marrow. This has led to the suggestion that Flt3-L, perhaps expressed constitutively by bone marrow fibroblasts, is a normal regulator of B cell lymphopoiesis, while cytokines produced by activated lymphocytes synergize with Flt3-L in times of stress to accelerate B cell development.

In addition to its effects on hematopoietic cells and B cells, Flt3-L has also been shown to stimulate the production of dendritic cells, a highly specialized cell involved in antigen presentation and therefore, normal immunity. Also, with the observation that Flt3-L stimulates the production of dendritic cells, Flt3-L has been identified for potential use in the area of vaccines, both traditional delivery of heat killed or otherwise attenuated agents, as well as protein, peptide or DNA vaccines.

For additional information on Flt3-L, see, for example, Shurin et al., "FLT3: Receptor and Ligand. Biology and Potential Clinical Application", Cytokine & Growth Factor Reviews, Vol. 9, No. 1, pp. 37–48, 1998.

One of the problems associated with the hematopoietic growth factors such as G-CSF, GM-CSF, SCF and Flt3-L, is the need for multiple daily injections. This, in turn leads to another common disadvantage of current injectable therapies such as these, that being the creation of a saw-toothlike effect of plasma drug levels. This is due to the creation of large bolus bursts of drug shortly after injection, leading to supraphysiologic levels of drug, followed by rapid drops in plasma drug levels as the drug is cleared from the body by normal clearance processes. Upon the next injection, the pattern is repeated with large spikes in plasma levels followed by sub-therapeutic levels until the next injection. An additional problem with current hematopoietic growth factor therapy includes fever and mild-to-moderate bone pain in patients receiving high doses over a long period. In addition, local skin reactions and mild to moderate splenomegaly have been reported.

There is a significant need for improved formulations and methods for delivery of hematopoietic growth factors that address one or more of these problems, especially as treatments involving the use of hematopoietic growth factors continue to expand.

SUMMARY OF THE INVENTION

The present invention provides a method for delivering a hematopoietic growth factor or other active agent to a host for expanding, activating, committing or mobilizing pluripotent self-renewing and committed stem cells in the host. As will be appreciated, hematopoietic growth factors are such active agents that expand, activate, commit and/or mobilize at least hematopoietic stem cells. The method of the invention is described herein with primary reference to hematopoietic growth factors, but the principles discussed apply equally to other active agents or to active agents administered for the purpose of expanding, activating, committing and/or mobilizing pluripotent self-renewing and committed stem cells other than hematopoietic stem cells.

The method of the present invention can be used to effect sustained delivery of a hematopoietic growth factor, thereby advantageously increasing the plasma half-life of of hematopoietic growth factor, and thereby also reducing the number of administrations, and therefore the number of injections, required for treatment. Moreover, the saw-tooth profiles of drug plasma levels experienced conventionally should be reduced with less frequent administrations, as should side effects caused by the frequent injections with conventional treatments. Furthermore, it has been found in at least some cases, that the activity of the hematopoietic growth factor is significantly improved with the method of the present invention, relative to conventional techniques. Therefore, not only should fewer administrations be required for a treatment program, but less hematopoietic growth factor should also be required in many instances, which would be expected to generally reduce the severity of side effects.

In one aspect, the method of the present invention for delivering a hematopoietic growth factor involves administering to a host a hematopoietic delivery composition. matopoietic growth factor delivery composition comprising a hematopoietic growth factor, a first biocompatible polymer, a second biocompatible polymer and a liquid vehicle. The first biocompatible polymer and the liquid vehicle interact in such a manner and are present in such proportions that the composition exhibits reverse-thermal viscosity behavior, in that the viscosity of the composition increases with increasing temperature over at least some temperature range. The second biocompatible polymer is a protective colloid.

The reverse-thermal viscosity behavior of the delivery composition permits the delivery composition to be administered to a host as a lower-viscosity flowable medium, which then converts to a higher-viscosity form in vivo. The hematopoietic growth factor is then advantageously released in a sustained manner from the protective environment of the higher-viscosity form of the delivery composition. To accomplish this result, the delivery composition should exhibit reverse-thermal viscosity behavior over at least some temperature range below the physiologic temperature of the host. The presence of the second biocompatible polymer helps to protect the composition from premature degradation in vivo due to invasion by aqueous biological fluids, such as are encountered by the delivery composition inside the host after administration. The inclusion of the second biocompatible polymer, therefore, is important to help protect the delivery composition so that the delivery composition can successfully make the transition from the lower-viscosity flowable medium to the higher-viscosity form following administration. Also, the second biocompatible polymer helps to inhibit premature deterioration in vivo of the higher-viscosity form, thereby promoting a prolonged release of the hematopoietic growth factor. Surprisingly, the inclusion of the second biocompatible polymer has also resulted in an observed significant increase in the activity of the hematopoietic growth factor under at least some circumstances. Although the mechanism of this enhancement is not well understood, the enhancement in activity of the observed hematopoietic growth factor with the composition is significant and surprising.

In one embodiment, the delivery composition that is administered to the host exhibits a reverse-thermal gelation property, which is a special case of reverse-thermal viscosity behavior in which the higher-viscosity form of the delivery composition is a gel (i.e., gelatinous substance). In this preferred embodiment of the delivery composition, the composition should have a reverse-thermal liquid-gel transition temperature that is no higher than the physiologic temperature of the host. In this situation, the composition is administered to the host as a flowable medium at a chilled temperature, and as the delivery composition warms in the host following administration the delivery composition converts to the gel form. Because the gel form is typically substantially immobile, the hematopoietic growth factor is released within the host at the desired location from the protective environment of the gel to facilitate sustained delivery of the hematopoietic growth factor.

In one preferred embodiment of the method, the delivery composition is in the form of a flowable medium at least at a first temperature and in the gel form at least at a second temperature that is higher than the first temperature, but not higher than the physiologic temperature of the host. In this way, the delivery composition is delivered to the host at the first temperature when the delivery composition is in the form of a flowable medium, and after administration, the delivery composition converts to the gel form as the temperature of the delivery composition increases within the host. For example, when the delivery composition is intended for use by a human host, the first temperature could advantageously be below 20° C., preferably in a range of 10° C. to 20° C., and the second temperature could advantageously be in a range of 25° C. to 37° C. In any event, with a human host the delivery composition should be preferably in the gel form at 37° C. Also, at the first temperature, the first biocompatible polymer is preferably substantially entirely dissolved in the liquid vehicle in the form of a solution that is liquid and flowable to an extent to impart sufficient fluidity to the delivery composition so that the delivery composition is administrable to a host by injection. The hematopoietic growth factor may also be dissolved in the solvent, or may be in the form of a fine precipitate suspended by the hematopoietic growth factor/solvent solution. The second biocompatible polymer will typically be in the form of a "colloidal solution" in the liquid vehicle, at least at the first temperature.

Also, for enhanced performance, the hematopoietic growth factor should be uniformly dispersed throughout the gel at the time of administration, which can typically be accomplished by mixing the composition at a temperature at which the first biocompatible polymer/liquid vehicle combination is in the form of a flowable liquid solution of the first biocompatible polymer in the liquid vehicle. In this way the hematopoietic growth factor can be dissolved in or uniformly dispersed throughout the solution, and then the temperature of the composition can be raised to convert the composition to the gel form for storage prior to use.

Both the foregoing summary description and the following detailed description are exemplary and are intended to provide explanation of the invention as claimed. Other aspects and novel features will be readily apparent to those skilled in the art from the following detailed description of the invention.

DETAILED DESCRIPTION

Figure 1:
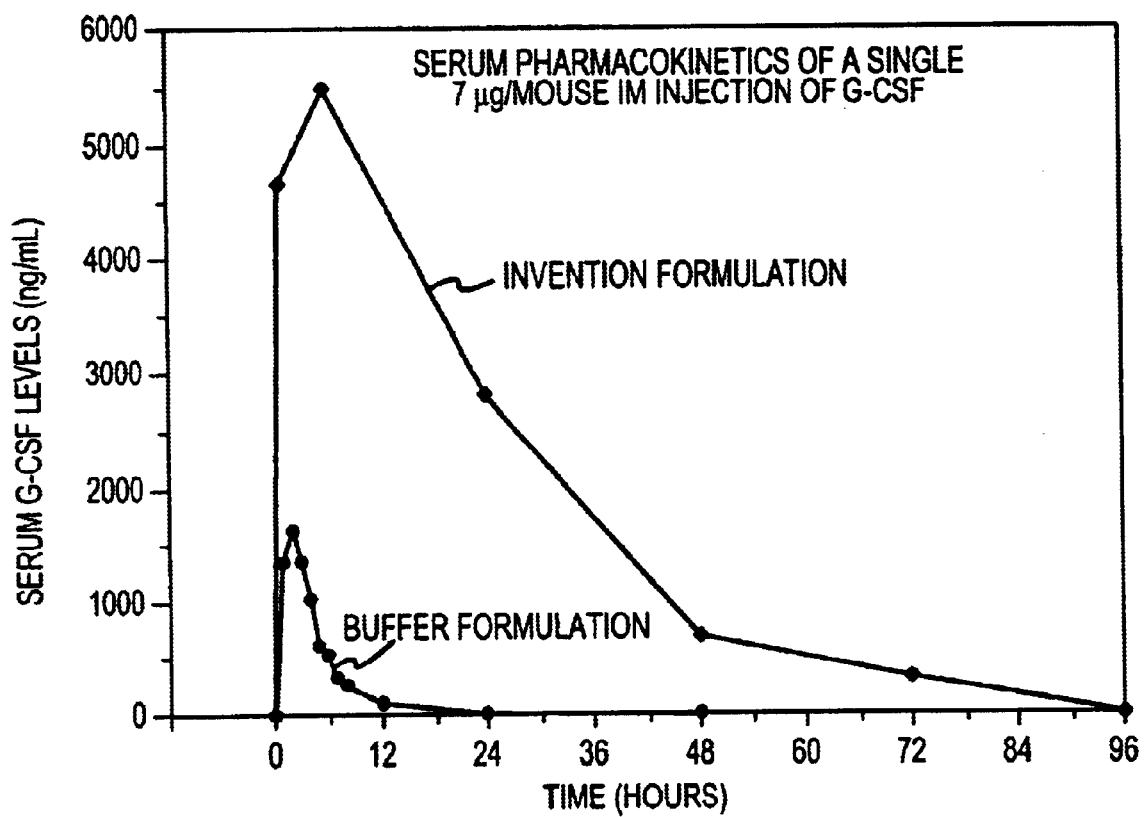
FIG. 1 is a plot in relation to Example 2 showing pharmacokinetic profiles of G-CSF formulated in buffer (Buffer Formulation) and according to one embodiment of the invention (Invention Formulation) described in Table 1. G-CSF in each of the formulations was administered to Balb/c mice as a single intramuscular (i.m.) injection containing 7 µg G-CSF. The concentration of G-CSF in serum was measured via ELISA. Reported are averages of serum G-CSF levels in 4 mice per sampling time.

As used herein, "CFU" means colony forming unit, "CFU-GEMM" means colony forming unit-granulocyte, erythrocyte, megakaryocyte, macrophage, "CFU-G" means colony forming unit-granulocyte, "CFU-GM" means colony forming unit-granulocyte-macrophage, "CFU-E" means colony forming unit-erythroid, "CFU-MK" means colony forming unit-megakaryocyte, and "CFU-Eo" means colony forming unit-eosinophil.

As use herein, "BFU" means burst forming unit, "BFU-E" means burst forming unit-erythroid, and "BFU-MK" means burst forming unit-megakaryocyte.

As used herein, "IL" means interleukin.

As used herein, "EPO" means erythropoietin.

As used herein "TPO" means thrombopoietin,

As used herein, "CSF" means colony stimulating factor, "G-CSF" means granulocyte colony stimulating factor, "M-CSF" means macrophage colony stimulating factor, and "GM-CSF" means granulocyte-macrophage colony stimulating factor.

As used herein, "CFC" means colony forming cells and "HPP-CFC" means high proliferative potential colony forming cells.

As used herein, "FGF" means fibroblast growth factor and "FGFb" means fibroblast growth factor basic.

As used herein, "LIF" means leukocyte inhibitory factor The terms "reverse-thermal viscosity property" and "reverse-thermal viscosity behavior" each refer to a property of a material, such as the first biocompatible polymer or the delivery composition as the case may be, to undergo a viscosity increase with increasing temperature across at least some temperature range.

As used herein, "reverse-thermal gelation property" refers to a property of a material, such as the first biocompatible polymer or the delivery composition, as the case may be, to change from a flowable medium, typically a liquid form, to a gel form as the temperature is raised from below to above a reverse-thermal liquid-gel transition temperature.

As used herein, "reverse-thermal liquid-gel transition temperature refers to a temperature at which, or a temperature range across which, a material, such as the first biocompatible polymer or the delivery composition, as the case may be, changes physical form from a flowable medium, typically a liquid form, to a gel form, as the temperature of the material is increased.

The term "reverse-thermal gelation polymer" refers to a polymer capable of interacting with a liquid vehicle so that the polymer/liquid vehicle combination exhibits a reverse-thermal gelation property at least at some proportions of the polymer and the liquid vehicle.

As used herein, "biocompatible" means not having toxic or injurious effects on biological function in a host.

As used herein, "protective colloid" means a hydrophilic polymer that has colloidal-size molecules and that is capable of interacting with water molecules through hydrogen bonding. By "colloidal-size," it is meant that one or more of the molecular dimensions when dispersed in an aqueous liquid are in a range of one nanometer to one micrometer.

The present invention provides a composition for delivery of hematopoietic growth factor to a biologic host, preferably a mammalian host, and more preferably a human host. The composition comprises at least one hematopoietic growth factor, at least one liquid vehicle, at least a first biocompatible polymer and at least a second biocompatible polymer that is different than the first biocompatible polymer. Optionally, the composition may also comprise additives such as penetration enhancers and protective stabilizers, and/or an active agent in addition to the hematopoietic growth factor.

The hematopoietic growth factor included in the delivery composition may be any material capable of stimulating hematopoietic cell activity in the intended host. The delivery composition may include only one type of hematopoietic growth factor or may include more than one different type of hematopoietic growth factors.

Exemplary hematopoietic growth factors useful in the delivery composition used with the method of the present invention include those in the multilineage group (including IL-3 and GM-CSF), the unilineage group (including EPO, G-CSF, IL-5, M-CSF and TPO) and the "potentiating" group (including IL-6, IL-11, LIF, FGF b, SCF and Flt3-L).

The amount of hematopoietic growth factor in the delivery composition varies depending on the nature and potency of the growth factor. In most situations, however, the amount of hematopoietic growth factor in the composition will be smaller than about 20% w/w relative to the first biocompatible polymer.

The present invention provides a method for delivering a hematopoietic growth factor for prolonged, or sustained, delivery of hematopoietic growth factor, thereby reducing the frequency of administrations as part of a treatment. Furthermore, it has been found that the method, in at least some circumstances, results in enhanced cell generation relative to the same quantity of hematopoietic growth factor administered by a conventional method. Not to be bound by theory, but to aid in the understanding of the invention, it is believed that the delivery composition reduces or eliminates degradation of the hematopoietic growth factor and allows for a relatively slow sustained administration of hematopoietic growth factors to the host. In addition, it is believed that use of the composition may be targetting the hematopoietic growth factor to tissues that would make the most efficient use of the hematopoietic growth factor.

The liquid vehicle may be any suitable liquid or mixture of liquids, but is typically an aqueous liquid. An important aspect of the delivery composition is that the liquid vehicle and the first biocompatible polymer are selected and included in the delivery composition in such proportions that the delivery composition exhibits reverse-thermal viscosity behavior over at least some temperature range. Therefore, the viscosity of the delivery composition increases with increasing temperature over some temperature range. At a first temperature within the temperature range, the delivery composition is in a lower-viscosity form, in which the delivery composition is in the form of a flowable medium. At a second temperature in the temperature range, which second temperature is higher than the first temperature, the delivery composition is in a higher-viscosity form that has a significantly higher-viscosity than the lower-viscosity form. Preferably the viscosity of the higher-viscosity form is at least 1 times, more preferably at least 2 times, and even more preferably at least 3 times as great as the viscosity of the lower-viscosity form. Advantageously, the first temperature is below the physiologic temperature of the host and the second temperature is at or below the physiologic temperature of the host. In this way, the delivery composition is administerable to the host as a flowable medium in the lower-viscosity form at a chilled temperature, with the delivery composition converting to the higher-viscosity form as the delivery composition warms up inside the host following administration. By "flowable," it is meant that the delivery composition is sufficiently fluid so as to be syringable.

The first biocompatible polymer in the delivery composition typically is a reverse-thermal gelation polymer. The first biocompatible polymer and the liquid vehicle are selected, and the delivery composition is formulated with relative proportions of the liquid vehicle and the first biocompatible polymer, so that the delivery composition exhibits reverse-thermal viscosity behavior across at least some temperature range, preferably a temperature range below 40° C., more preferably a temperature range below 37° C. and even more preferably a temperature range within a range of from 10° C. to 37° C. Typically, the delivery composition exhibits reverse-thermal viscosity behavior over at least some temperature range within a range of 1° C. to 20° C. Due to the reverse thermal viscosity behavior of the delivery composition, the delivery composition can be administered to the host at a cooler temperature where the composition has a lower-viscosity, with the viscosity of the composition then increasing in the host following administration, whereby the mobility of the composition is severely reduced within the host following administration. In one embodiment, in the case of a human host, the delivery composition is preferably in the form of the lower-viscosity flowable medium at least at a first temperature at or below 20° C., and more preferably in a range of 1° C. to 20° C., and the delivery composition is preferably in the higher-viscosity form at least at a second temperature in a range of from 25° C. to 37° C.

In one preferred embodiment, the liquid vehicle and first biocompatible polymer are selected and included in the delivery composition in such proportions that the delivery composition has a reverse-thermal gelation property, so that the higher-viscosity form is a gel. In this situation, the delivery composition should have a reverse-thermal liquid-gel transition temperature that is no higher than the physiologic temperature of the host, but that is high enough to be convenient for administration to the host in the form of a flowable medium.

When the delivery composition has a reverse thermal gelation property, then the delivery composition will exist in the form of a flowable medium at least at a first temperature and in the form of a gel at least at a second temperature that is higher than the first temperature. Preferably both the first and second temperatures are below 40° C., and more preferably the second temperature is no higher than 37° C., especially in the case of a human host. A preferred situation is when the first temperature is in a range of 1° C. to 20° C. and the second temperature is in a range of 25° C. to 37° C.

Any first biocompatible polymer may be used that, as formulated in the delivery composition, is capable of interacting with the liquid vehicle to impart the desired reverse-thermal viscosity behavior to the delivery composition. Non-limiting examples of some reverse-thermal gelation polymers useful for preparing the delivery composition include certain polyethers (preferably polyoxyalkylene block copolymers with more preferred polyoxyalkylene block copolymers including polyoxyethylene-polyoxypropylene block copolymers referred to herein as POE-POP block copolymers, such as Pluronic™ F68, Pluronic™ F127, Pluronic™ L121, and Pluronic™ L101, and Tetronic™ T1501); certain cellulosic polymers, such as ethylhydroxyethyl cellulose; and certain poly (ether-ester) block copolymers (such as those disclosed in U.S. Pat. No. 5,702,717). Pluronic™ and Tetronic™ are trademarks of BASF Corporation. Furthermore, more than one of these and/or other biocompatible polymers may be included in the delivery composition to provide the desired characteristics and other polymers and/or other additives may also be included in the delivery composition to the extent the inclusion is not inconsistent with performance requirements of the delivery composition. Furthermore, these polymers may be mixed with other polymers or other additives, such as sugars, to vary the transition temperature, typically in aqueous solutions, at which reverse-thermal gelation occurs.

Polyoxyalkylene block copolymers are particularly preferred to use as the biocompatible reverse-thermal gelation polymer. A polyoxyalkylene block copolymer is a polymer including at least one block (i.e. polymer segment) of a first polyoxyalkylene and at least one block of a second polyoxyalkylene, although other blocks may be present as well. POE-POP block copolymers are one class of preferred polyoxyalkylene block copolymers for use as the biocompatible reverse-thermal gelation polymer in the delivery composition. POE-POP block copolymers include at least one block of a polyoxyethylene and at least one block of a polyoxypropylene, although other blocks may be present as well. The polyoxyethylene block may be represented by the formula $(C_2H_4O)_b$ when b is an integer. The polyoxypropylene block may be represented by the formula $(C_3H_6O)_a$ when a is an integer. The polyoxypropylene block could be for example $(CH_2CH_2CH_2O)_a$, or could be

Several POE-POP block copolymers are known to exhibit reverse-thermal gelation properties, and these polymers are particularly preferred for imparting reverse-thermal viscosity behavior properties to the delivery composition. Examples of POE-POP block copolymers include Pluronic™ F68, Pluronic™ F127, Pluronic™ L121, Pluronic™ L101, and Tetronic™ T1501. Tetronic™ T1501 is one example of a POE-POP block copolymer having at least one polymer segment in addition to the polyoxyethylene and polyoxypropylene segments. Tetronic™ T1501 is reported by BASF Corporation to be a block copolymer including polymer segments, or blocks, of ethylene oxide, propylene oxide and ethylene diamine.

As will be appreciated, any number of biocompatible polymers may now or hereafter exist that are capable of imparting the desired reverse-thermal viscosity behavior to the delivery composition, and such polymers are specifically intended to be within the scope of the present invention when incorporated into the delivery composition for use with the method of the invention.

Some preferred POE-POP block copolymers have the formula:

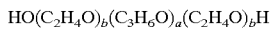

which, in the preferred embodiment, has the property of being liquid at ambient or lower temperatures and existing as a semi-solid gel at mammalian body temperatures wherein a and b are integers in the range of 15 to 80 and 50 to 150, respectively. A particularly preferred POE-POP block copolymer for use in the delivery composition has the following formula:

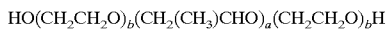

wherein a and b are integers such that the hydrophobe base represented by $(CH_2(CH_3)CHO)_a$ has a molecular weight of about 4,000, as determined by hydroxyl number; the polyoxyethylene chain constituting about 70 percent of the total number of monomeric units in the molecule and where the copolymer has an average molecular weight of about 12,600 atomic mass units (amu) or Daltons. Pluronic™ F-127, also known as poloxamer 407, is such a material. In addition, a structurally similar Pluronic™ F-68 may also be used.

The procedures used to prepare aqueous solutions which form gels of polyoxyalkylene block copolymer are well known and are disclosed in U.S. Pat. No. 5,861,174, which is incorporated herein by reference in its entirety. Typically, the amount of polymer and the amount of hematopoietic growth factor are selected such that the resulting composition has reverse-thermal gelation properties at a transition temperature at less than about 37° C., preferably between about 10° C. and 37° C., more preferably between about 20° C. to about 37° C. The concentration of the first biocompatible polymer in the composition will vary depending upon the specific first biocompatible polymer and the specific situation. In most situations, however, the first biocompatible polymer will comprise from about 1% by weight to about 70% by weight, and more typically from about 10% by weight to about 33% by weight. For example, particularly preferred for Pluronic™ F-127 is a range of from about 13% by weight to about 25% by weight.

The second biocompatible polymer is a protective colloid, and is included to impart increased resistance of the delivery composition to physical deterioration that might otherwise occur then the delivery composition encounters extraneous aqueous liquids. This is particularly important to protect the higher-viscosity form, such as the gel, from premature structural deterioration due to the influence of aqueous biological fluids following administration to the host. In particular, the first biocompatible polymer is subject to dissolution in aqueous biological liquids encountered after administration of the delivery composition to the host. The second biocompatible polymer helps to inhibit or prevent such dissolution of the first biocompatible polymer, thereby helping to maintain the structural integrity of the delivery composition in vivo.

The second biocompatible polymer is hydrophilic. Preferably, the second biocompatible polymer is more hydrophilic than the first biocompatible polymer. By having a higher affinity for water than the first biocompatible polymer, the second biocompatible polymer tends to protect the first biocompatible polymer from being dissolved away by aqueous biological fluids present in the host. The protection afforded by the second biocompatible polymer helps to inhibit deterioration of the delivery composition, so that the higher-viscosity form of the delivery composition will endure for some significant time following administration, permitting delivery of the hematopoietic growth factor to be sustained over an extended time. Absent the second biocompatible polymer, the first biocompatible polymer would be much more susceptible to dissolution by biological fluids, which could, for example, prematurely destroy integrity of the desired gel character of the high-viscosity form of the delivery composition.

Also, the second biocompatible polymer is of colloidal molecular size and of high molecular weight. Typically, the weight average molecular weight of the second biocompatible polymer is at least 5,000 Daltons and more typically, at least 10,000 Daltons. In many situations, the second biocompatible polymer has a weight average molecular weight of at least 50,000 and often 100,000 or more.

The second biocompatible polymer can be any biocompatible polymer that acts as a protective colloid in the delivery composition. The second biocompatible polymer will, however, ordinarily be a saccharide-based polymer. By saccharide-based, it is meant that the second biocompatible polymer is a polysaccharide or a derivative of a polysaccharide material.

Cellulosic polymers are particularly preferred for use as the second biocompatible polymer, and especially preferred are cellulosic polymers that are swellable by water. Non-limiting examples of cellulosic polymers for use as the second biocompatible polymer include methylcellulose, hydroxymethylcellulose, hydroxyethylcellulose, hydroxypropylcellulose, hydroxypropyl methylcellulose, ethyl hydroxyethyl cellulose and carboxymethyl cellulose. A particularly preferred cellulosic polymer for use as the second biocompatible polymer is hydroxypropyl methylcellulose.

Also useful as the second biocompatible polymer are phycocolloids. A phycocolloid is a hydrophilic carbohydrate polymer occurring in algae, and derivatives of such polymers. Some examples of phycocolloids include carrageenan, algin, and agar. Also useful as the second biocompatible polymer are alginates such as, for example, sodium alginate.

The hematopoietic growth factor, liquid vehicle, first biocompatible polymer and second biocompatible polymer can be present in the delivery composition in any suitable relative proportions compatible with the performance requirements of the delivery composition. Typically, however, the delivery composition will include from 0.00000001 weight percent to 0.000005 weight percent of the hematopoietic growth factor, from 60 weight percent to 96 weight percent of the liquid vehicle, from 5 weight percent to 33 weight percent of the first biocompatible polymer and from 0.1 weight percent to 5 weight percent of the second biocompatible polymer.

The delivery can also comprise other additives, including polymer or protein stabilizers such as glycerol, trehalose, sucrose, glycine, mannitol, and albumin.

In one embodiment, the composition may optionally also include an active agent, in addition to the hematopoietic growth factor, that is to be delivered to a host along with the hematopoietic growth factor. In one preferred embodiment, the composition is used for vaccination purposes, and the composition includes an antigen in addition to the hematopoietic growth factor. As used herein, antigen refers to any substance or material capable of causing an immune response when administered to a host. Antigens include, for example, polypeptides, peptides, proteins, glycoproteins and polysaccharides that are obtained from animal, plant, bacterial, viral protozoan and parasitic sources or are produced by synthetic methods, including epitopes of proteins.

Exemplary antigens which may be included in the delivery composition include antigens from bacteria, protozoa and viruses against which vaccines are currently available or later developed, such as antigens from viruses, protozoa or bacteria that are the causative agents of childhood illnesses, Tetanus toxoid, Diphtheria toxoid and other non-pathogenic mutants of these toxins, antigens from *Bordatella pertussis*, antigens from *M. tuberculosis*, antigens from *P. falciparum*, antigens from blood-borne pathogens including Hepatitis C antigens, and HIV antigens; tumor-specific antigens; and antigens derived from HCG or other molecules involved in the mammalian reproductive cycle. Preferably the antigen is selected from the group consisting of tetanus toxoid, diphtheria toxoid and other non-pathogenic mutants of these toxins, other antigens from viruses or bacteria that are the causative agents of childhood illnesses, antigens from *M. tuberculosis*, antigens from *Bordatella pertussis*, antigens from viruses or bacteria against which vaccines are currently available, Hepatitis C antigens, HIV antigens and antigens from other blood-borne pathogens and tumor-specific antigens. Most preferably the antigen is selected from the group consisting of Tetanus toxoid, Diphtheria toxoid and other non-pathogenic mutants of these toxins, other antigens from viruses or bacteria that are the causative agents of childhood illnesses, antigens from M tuberculosis, antigens from *Bordatella pertussis* or HIV and antigens from viruses or bacteria against which vaccines are currently available. Particularly preferred is for the antigen to include one or more of tetanus toxoid, diphtheria toxoid and antigens from *Bordatella pertussis*.

When an antigen is used, the amount of antigen in the delivery composition varies depending on the nature and potency of the antigen. Typically, however, the amount of antigen present in the delivery composition is from about 0.000001% by weight of the composition to about 5% by weight of the composition.

According to the invention, the delivery composition may be administered to a host to achieve any desired hematopoietic effect. Preferably the host is a mammal, and more preferably a human. The composition can be administered in a variety of forms adapted to the chosen route of administration, e.g., parenterally. Parenteral administration in this respect includes administration by the following routes: intravenous, intramuscular, subcutaneous, intrasynovial, transepithelially including transdermal, sublingual and buccal, intranasal, and intraperitoneal. Preferably, the mode of administering the delivery composition is selected from the group consisting of subcutaneous and intramuscular injections, and mucosal routes, including intranasal, with injection routes being even more preferred.

The composition is typically prepared in water, a saline solution or another aqueous liquid as the liquid vehicle. Under ordinary conditions of storage and use, these preparations can also contain a preservative to prevent the growth of microorganisms. The composition suitable for injectable use includes sterile aqueous solutions. Preferably, the composition is sterile with sufficient fluidity for easy syringability. It can be stable under the conditions of manufacture and storage and preferably preserved against the contaminating action of microorganisms such as bacterial and fungi. The liquid vehicle can be a solvent of dispersion medium containing, for example, water, ethanol, polyol (e.g., glycerol, propylene glycol, and liquid polyethylene glycol, and the like), and suitable mixtures thereof. The proper fluidity can be maintained, for example, by maintaining the temperature of the composition having reverse-thermal gelation properties below the transition temperature. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars, phosphate buffers, sodium chloride, or mixtures thereof.

According to the method of the invention, the delivery composition can be implanted directly into the body by injecting it as a liquid, whereupon the composition will ordinarily gel as it warms inside the body when the composition has reverse-thermal gelation properties. Also, although the delivery composition is typically sufficiently fluid and flowable when administered, it will convert to a semi-solid gel inside the host when it has the proper reverse-thermal gelation properties. Also, the composition can be administered in the form of a gel, for example by surgical implantation of the gel.

In another embodiment, solutes, can be incorporated into the delivery composition, for example to stabilize the hematopoietic growth factor. The use of such protein-stabilizing solutes, such as, for example, sucrose, not only aid in protecting and stabilizing the protein (i.e., hematopoietic growth factor), but also allow the first biocompatible polymer to form suitable gels at lower concentrations than needed in water or buffer alone and/or to change the transition temperature at which reverse-thermal gelation occurs. Thus, the working range of first biocompatible polymer concentration can be widened and the transition temperature modified. It is known that in some cases a gel will not form when the concentration of polyoxyethylene-polyoxypropylene block copolymer in water or dilute buffer is outside a particular range, e.g., equal to or less than 15% percent by weight for some such polymers. However, by introducing protein-stabilizing solutes into the delivery composition, the transition temperature may be manipulated, while also lowering the concentration of polyoxyethylene-polyoxypropylene block copolymer that is necessary to form a gel.

The delivery composition can be used to stimulate hematopoietic cell activity by administering the growth factor delivery composition to a host by any suitable administration technique. Typically, the delivery composition is chilled at the time of administration so as to be in the form of a flowable medium. Also, the first biocompatible polymer, and the hematopoietic growth factor, is preferably substantially entirely dissolved in the liquid vehicle when administered to the host.

As noted, the delivery composition can be formulated for use with the method of the present invention to include any active agent capable of expanding, activating, committing and/or mobilizing one or more pluripotent, self-renewing and committed stem cells. One preferred type of such pluripotent, self-renewing and committed stem cells to be expanded, activated, committed or mobilized with the present invention are CD34+cells. Another preferred type of such pluripotent, self-renewing and committed stem cells to be expanded, activated, committed or mobilized with the present invention are CFU-GM's.

Some preferred active agents are cytokines, such as for example those selected from the group consisting of a cytokine selected from the group consisting of granulocyte colony-stimulating factor (G-CSF), stem cell factor, granulocyte-macrophage colony-stimulating factor (GM-CSF), macrophage colony-stimulating factor (M-CSF), stem cell factor (SCF), interleukin-1 (IL-1), interleukin-2 (IL-2), interleukin-3 (IL-3), interleukin-4 (IL-4), interleukin-6 (IL-6), interleukin-7 (IL-7), interleukin-8 (IL-8), interleukin-11 (IL-11), interleukin-12 (IL-12), Flt3-L, TPO and EPO. Also, in one embodiment, the delivery composition comprises a plurality of these or other cytokines that together have additive or synergistic properties for effects. In one embodiment the active agent comprises a chemokine.

Furthermore, the method of the invention can be applied to use the delivery composition for a variety of applications. One application is for administration of the delivery composition following injection of one or more chemotherapeutic drug, such as 5-fluorouracil. Another application involves, after administering the delivery composition, collecting pluripotent, self-renewing and committed stem cells from the host for later return to the host following some intermediate procedure, typically after enrichment (such as by immunoadsorption using an antibody for at least a portion of the pluripotent, self-renewing cells). The collecting can for example involve collecting peripheral blood by leukapheresis. The intermediate administration could be, for example, chemotherapy, radiotherapy, a bone marrow transplant, a peripheral blood leukocyte transplant from a human donor, and HIV therapy. Another application involves administering the delivery composition after a medical procedure, such as those procedures listed in the prior sentence. For example, in the case of a bone marrow transplant, administration of the delivery composition can improve engraftment. After undergoing a peripheral blood leukocyte transplant, administering the delivery composition can improve engraftment of the peripheral blood leukocyte transplant. Also, the delivery composition may be delivered as part of an administration regimen involving a plurality of administrations. For example, some applications may involve daily administrations for up to 200 days. In one application, the host is suffering from a hematopoietic disorder and the delivery composition is administered to as part of a treatment for the disorder. For example, the hematopoietic disorder could be a side effect of radiation therapy, chemotherapy a bone marrow transplant or another medical procedure. For example, the hematopoietic disorder could be a side effect of chemotherapy or radiation therapy, such as neutropenia, anemia, thrombocytopenia, or immune dysfunction. Or the hematopoietic disorder could be for example a congenital or neoplastic associated neutropenia, neutropenia associated with HIV therapy, or neutorpenia from some other cause. Any appropriate active agent or combination of active agents can be used as appropriate for the particular situation. For example, interleukin-7 (IL-7) is a preferred active agent for administration following a bone marrow transplant.

Moreover, active agents (e.g., mobilizing cytokines) useful with the present invention have been used for example for significantly increasing CD34 cells and CFU-GM's in the peripheral blood. They have also used, for myelorestorative properties. However, there are significant deficiencies to the use of conventional saline formulated cytokines including pharmacokinetic liabilities. Further, there are multiple reasons to use a cytokine or a combination of cytokines within a formulation for mobilization. First, approximately 40% of patients are considered poor mobilizers requiring an excessive number of apheresis to obtain sufficient CD34 cells for transplantation. Indeed, a significant number of patients who have had four or more cycles of chemotherapy, are unable to be mobilized despite the use of both apheresis and bone marrow products. Thus, a strategy, such as the method of the present invention that improves mobilization would have a significant impact on these "poor" mobilizers. Any approach that would improve mobilization and reduce the number of apheresis sessions would be both cheaper and therapeutically attractive. Further, any increase in the number of CD34+ cells available for transplantation will improve hematopoietic recovery following transplantation. Indeed, there may be a direct correlation between the number of CD34+ cells infused and overall survival following transplantation.

Also, cytokines and growth factors, principally both G-CSF and GM-CSF have also shown significant activity in reducing days on antibiotics, frank culture-positive infections and days with fever following both conventional dose and high-dose chemotherapy and in some instances for the successful treatment of cyclic neutropenia, MDS etc. Thus, the use of the method of the present invention with the delivery composition that delivers a cytokine with fewer number of injections and increased activity has significant potential for use as an anti-infective therapeutic. Further, activity in restoring neutrophils, platelets, immune function and or erythrocytes following transplantation, conventional dose therapy or myelosuppressive therapy such as anti-retroviral drugs for HIV treatment provides additional indications. Thus, the use of cytokines within slow release formulations will also have anti-infective activity, at least for those microbes that can be controlled by neutrophils and potentially monocytes-histiocytes. Further, this may be due not only to a rapid resolution of neutropenia but also activation of cellular effectors via the up-regulation of bacteriostatic enzymes, or nonspecific activation of both neutrophils and monocytes.

The use of the delivery composition with the method of the present invention provides an important new approach to increasing the duration of action of cytokines in vivo. The use of these formulations significantly alters pharmacokinetic and pharmacodynamic properties and can significantly improve the length of time that molecules remain effective in the circulation. Such formulated cytokines have prolonged clearance, increased half-life and sustained biological activity when compared to their saline formulated counterparts. Therapeutic potential includes treatment of neutropenia; including chemotherapy associated, congenital and drug induced; mobilization of pluripotent, stem and progenitor cells; treatment of infections in addition to associated indications. The increased activity associated with these formulations, opens new indications in addition to those patients who are refractory to treatment with current drugs due to co genetic or iatrogenic neutropenia.

EXAMPLES

Additional objects, advantages, and novel features of this invention will become apparent to those skilled in the art upon examination of the following examples thereof, which is not intended to be limiting.

Example 1

Formulation of G-CSF with Pluronic™ F127

In one preferred embodiment of the present invention, the hematopoietic growth factor is G-CSF, and the delivery composition of the present invention provides a delivery system for the sustained administration of G-CSF to a human or animal host. A preferred first biocompatible polymer in this situation is a POE-POP block copolymer with reverse-thermal gelation properties.

As a specific formulation example, G-CSF can be formulated with Pluronic™ F127 (poloxamer 407), with and without hydroxypropylmethylcellulose (HPMC). Dry powder forms of Pluronic™ F127 and HPMC are weighed, mixed together, and then reconstituted in water or physiological buffer to achieve the drug delivery matrix containing, upon addition of G-CSF, the desired concentrations of each component. More specifically, the concentration of Pluronic™ F127 is one that will achieve a final concentration (e.g., 5–30 weight %) at which it forms a semi-solid gel, along with the addition of HPMC, at body temperature (37° C.). If included, HPMC can be added in an amount to achieve a final concentration (e.g., HPMC 0.1–5 weight %) necessary to modulate the physicochemical or pharmacological properties of the Pluronic™ F127 or G-CSF. Alternatively, Pluronic™ F127 and HPMC can be formulated separately as individual solutions and then mixed together to produce the drug delivery matrix containing, upon addition of G-CSF, the desired concentrations of each component. As a further alternative, a solution of either Pluronic™ F127 or HPMC in buffer or water and a dry powder of the second polymer (i.e., either Pluronic™ F127 or HPMC) can be mixed together to achieve the drug delivery matrix containing, upon addition of G-CSF, the desired concentrations of each component.

G-CSF can be added to the liquid or dry mixture of Pluronic™ F127 and HPMC. The G-CSF can be added in dry powder form, or as a liquid solution to the drug delivery matrix. Final concentrations of G-CSF in the Pluronic™ F127 and HPMC drug delivery matrix include those concentrations that will provide biological levels of G-CSF as a sustained release following injection. For example, G-CSF can be added at a concentration so that the injected volume contains dosages of G-CSF that would provide therapeutic levels for a sustained period after administration. More specifically, G-CSF can be incorporated into the delivery matrix at various desired concentrations, such as for example, to provide 1 to 500 $\mu$g/injection of G-CSF.

The addition of HPMC in the delivery matrix modulates G-CSF in such a way that the pharmacokinetic profile is altered to provide sustained levels of G-CSF in serum compared to G-CSF in only Pluronic™ F127. Furthermore, addition of HPMC greatly increases the pharmacological action of G-CSF not only on peripheral blood hematopoeisis, but also on spleen and bone marrow cell hematopoeisis. Although the mechanism of action of HPMC on the pharmacokinetic profile and pharmacological action of G-CSF is not known, it is proposed that the addition of HPMC may 1) stabilize the delivery matrix, 2) stabilize the hematopoietic growth factor, 3) target the hematopoietic growth factor to its site of action within the body, and/or 4) enable the hematopoeitic growth factor to exert its hematopoeitic action on earlier progenitor cells either directly by the growth factor or indirectly by stimulating other cytokines or growth factors.

Example 2

Administration of G-CSF with Pluronic™ 127

Formulations including G-CSF, Pluronic™ 127, with and without HPMC, are prepared and administered to groups of Balb/c mice to determine a) the effect of formulating G-CSF in a Pluronic™ 127 and HPMC (Invention Formulation) delivery matrix on the pharmacokinetic profile of G-CSF compared to conventionally (Buffer Formulation) formulated G-CSF and b) the effects of the Invention Formulation on hematopoietic activity compared to conventionally formulated G-CSF. The formulations are administered to mice intramuscularly (i.m.), as a single dose for pharmacokinetic analysis and as either single (for Invention Formulation) or multiple (for Buffer Formulation) doses for hematopoeitic acitivity. The compositions of the formulations are shown in Table 1.

TABLE 1

| Group | Pluronic ™ F127 (% w/w) | G-CSF (μg/mL) | HPMC (% w/w) |
|---|---|---|---|
| Vehicle control, buffer | 0 | 0 | 0 |
| Vehicle control, gel | 17 | 0 | 0.1 to 5 |
| G-CSF in buffer (Buffer Formulation) | 0 | 1 to 300 | 0 |
| G-CSF with Pluronic ™ 127 and HPMC (Invention Formulation) | 17 | 7 to 100 | 0.1 to 5 |

Figure 2:
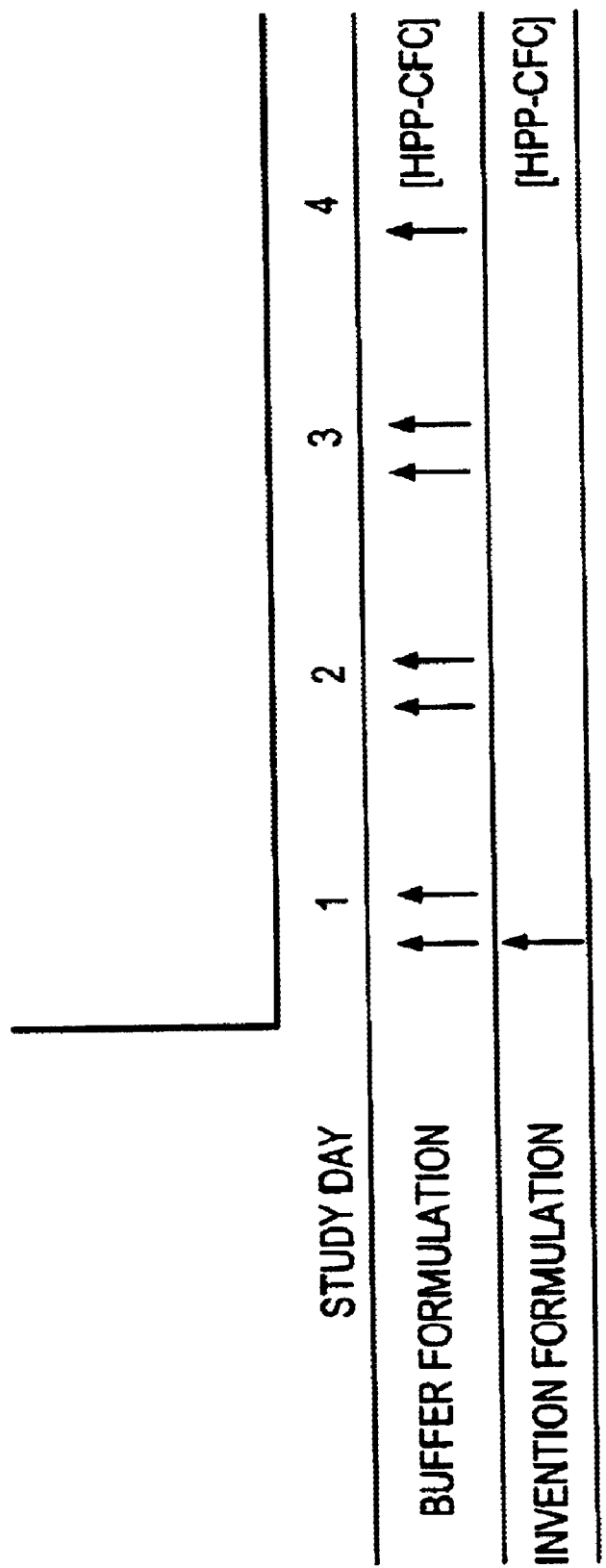
FIG. 2 is a timeline of the study design for Example 2 employed to assess the pharmacological action of G-CSF in mice. G-CSF in the Buffer Formulation was injected twice daily for 3 days and once the day of sampling for a total of 7 injections. G-CSF in the Invention Formulation was administered as a single injection on day 1 of the study with sampling at day 4. Injections were given intramuscularly (i.m.) to Balb-C mice.
Figure 3:
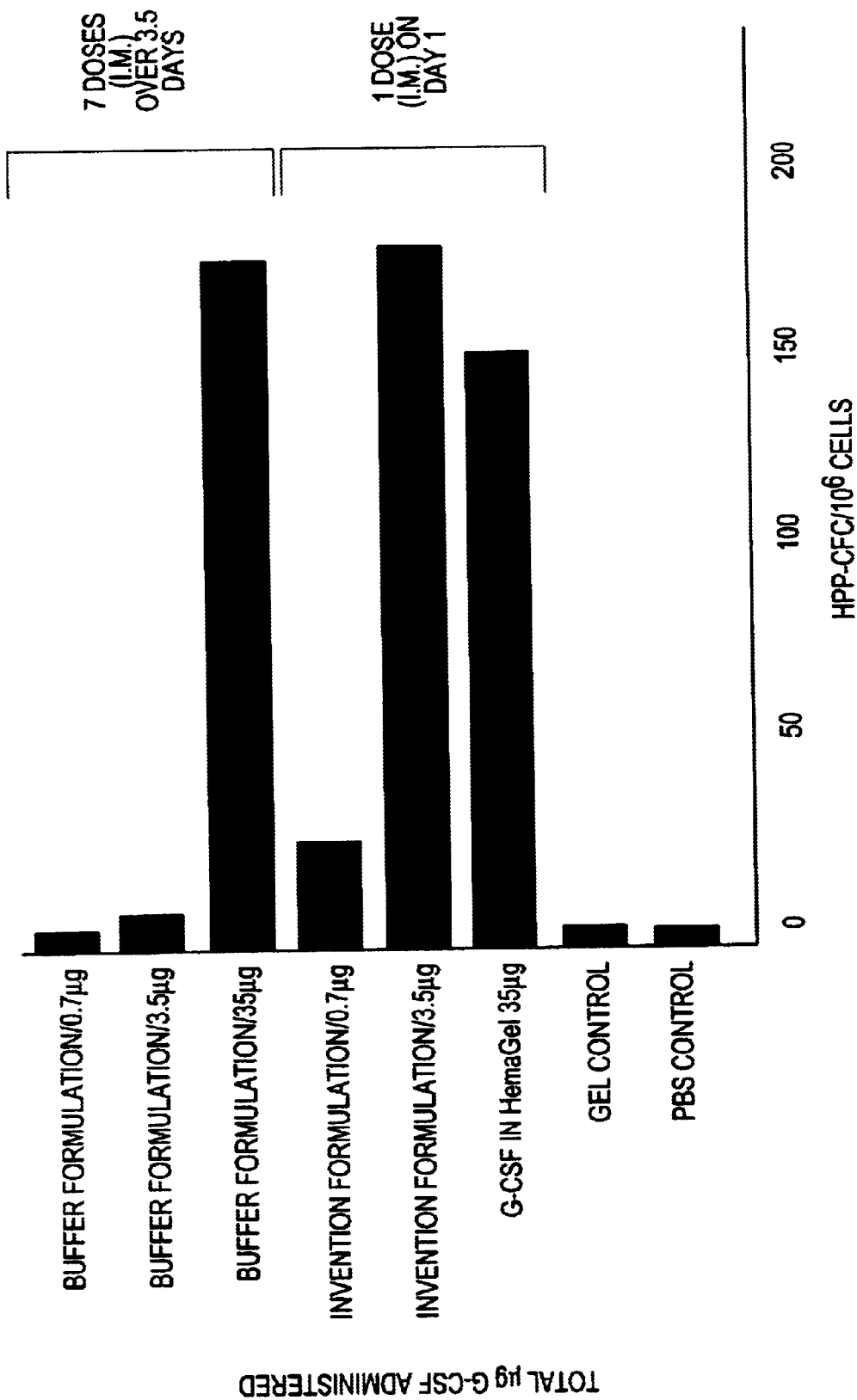
FIG. 3 is a bar graph in relation to Example 2 of the pharmacological action of G-CSF as determined by mobilization of HPP-CFC cells in peripheral blood. G-CSF in the Buffer Formulation was injected twice daily for 3 days and once the day of sampling for a total of 7 injections. Each injection contained either 0.1, 0.5, or 5.0 G-CSF for a total cumulative dose of 0.7, 3.5, or 35 µg G-CSF/mouse, respectively. G-CSF in the Invention Formulation was administered as a single injection on day 1 of the study with sampling at day 4. The single injection contained either 0.7, 3.5, or 35 µg G-CSF. Injections were given intramuscularly (i.m.) in Balb/c mice. Mobilization of HPP-CFC was determined by quantitating the number of HPP-CFC cells upon cytokine (IL-3)-stimulation of isolated peripheral blood leukocytes.

Two studies are performed. In the first study, Balb/c mice receive a single i.m. injection of 7 μg G-CSF in either the Buffer Formulation or the Invention Formulation. Blood is sampled at various timepoints for up to 96 h. G-CSF concentration in serum is determined via ELISA. The pharmacokinetic profile of G-CSF from the Buffer Formulation and the Invention Formulation are shown in FIG. 1. In the second study, a group of mice receive a single i.m. injection of G-CSF in the Invention Formulation at a dose of 0.7, 3.5 or 35 μg/mouse, and another group of mice receive 7 injections of G-CSF in the Buffer Formulation at a dose of 0.1, 0.5 or 5 μg/injection for a total cumulative dose of 0.7, 3.5 or 35 μg/mouse. The dosing schedule and study design for this second study is outlined in FIG. 2. The hematopoietic action of these two G-CSF formulations as well as vehicle controls was determined by assessing numbers of HPP-CFC cells in the peripheral blood leukocyte fraction 4 days after initiation of G-CSF injection. HPP-CFC cells were quantitated microscopically after performing colony forming assays of cytokine (IL-3)-stimulated peripheral blood leukocytes. The results of this second study are shown in FIG. 3.

To summarize the results in the two studies, G-CSF in the Invention Formulation:

(a) has a longer serum half-life; and
(b) increases HPP-CFC numbers in peripheral blood better than conventionally formulated and administered G-CSF.

The results show a substantial improvement in the delivery of G-CSF, using the Invention Formulation relative to the Buffer Formulation. Referring to FIG. 3, it is particularly surprising and noteworthy that the Invention Formulation administered in a single 3.5 μg of G-CSF injection increased the presence of HPP-CFC in peripheral blood by an amount comparable to the increase produced by 10 times as much G-CSF (35 μg) administered in a multi-injection regimen using the Buffer Formulation. The improvement in delivery of G-CSF can be seen in at least two specific ways: first by providing a more sustained pharmacokinetic profile (longer half-life) and second as creating an apparently more potent hematopoietic growth factor than is exhibited by conventional formulations. The importance of this can been viewed from a variety of perspectives, including:

(a) as a component to a marketed hematopoeitic growth factor, it would likely decrease dose costs of since less growth factor would likely be used to produce the same biological effect;
(b) from the patient perspective, if a total lower drug dosage is used, it would be expected to produce fewer side effects (which for hematopoeitic growth factors are often dose limiting, including fever and joint pain); and
(c) also from the patient perspective, a better pharmacokinetic profile leads to fewer injections per course of therapy.

Example 3

Formulation of Flt3-L with Pluronic™ F127

In a preferred embodiment of the present invention, the hematopoietic growth factor is Flt3-L, and the pharmaceutical composition of the present invention provides a delivery system for the sustained administration of the Flt3-L to a human or animal. A preferred first biocompatible polymer in this situation is a POE-POP block copolymer with reverse-thermal gelation properties.

As a specific formulation example, Flt3-L can be formulated with Pluronic™ F127 (poloxamer 407), with or without hydroxypropylmethylcellulose (HPMC). Pluronic F127 is initially formulated in water or physiological buffer at concentrations (e.g., 5–30%) at which it forms a semi-solid gel, along with the addition of HPMC, at body temperature (37° C.). HPMC may then be added to the Pluronic™ F127 formulation at concentrations necessary to modulate the physicochemical properties of the Pluronic™ F127. (e.g., final concentrations of HPMC 1–5%). Alternatively, Pluronic™ F127 and HPMC can be formulated separately as individual solutions and then mixed together to produce the drug delivery matrix containing, upon addition of Flt3-L, the desired concentrations of each component. As a further alternative, dry powder forms of Pluronic™ F127 and HPMC can be mixed together and then reconstituted in water or physiological buffer to achieve the drug delivery matrix containing, upon addition of Flt3-L, the desired concentrations of each component.

Flt3-L can be added to the liquid or dry mixture of Pluronic™ F127 and HPMC. The Flt3-L can be added in dry powder form, or as a liquid solution to the drug delivery matrix. Final concentrations of Flt3-L in the Pluronic™ F127 and HPMC drug delivery matrix include those concentrations that will provide biological levels of Flt3-L as a sustained release following injection. For example, Flt3-L could be added at concentrations ranging from about 3 to about 15 μg for proposed delivery of 1 to 5 μg per day over a 3 day sustained release.

The addition of HPMC modulates Flt3-L in this delivery formulation in such a way that although the pharmacokinetic profile of Flt3-L in serum is not altered compared to a drug delivery matrix containing only Pluronic™ F127, the biological activity of Flt3-L on spleen and bone marrow cell differentiation is significantly increased.

Example 4

Administration of Flt3-L with Pluronic™ 127

Formulations including Flt3-L, Pluronic™ 127 and, optionally, HPMC are administered to groups of Balb/c mice to determine a) the effects of the formulations on pharmacokinetics compared to conventionally formulated Flt3-L and b) the effects of the formulations on hematopoietic activity compared to conventionally formulated Flt3-L. The formulations are administered to mice i.m. as a single dose. The compositions of the formulations are shown in Table 2.

TABLE 2

| Group | Pluronic™ F127% w/w | Flt3-L (µg/mL) | HPMC %(w/w) |
|---|---|---|---|
| Vehicle control (aqueous buffer) | 0 | 0 | 0 |
| Flt-3L parent (Flt3-L formulated in aqueous buffer) | 0 | 150 | 0 |
| PGZ-1 (Flt3-L formulated in F127) | 22 | 150 | 0 |
| PGZ-2 (Flt3-L formulated in F127/HPMC) | 22 | 150 | 5 |

Figure 4:
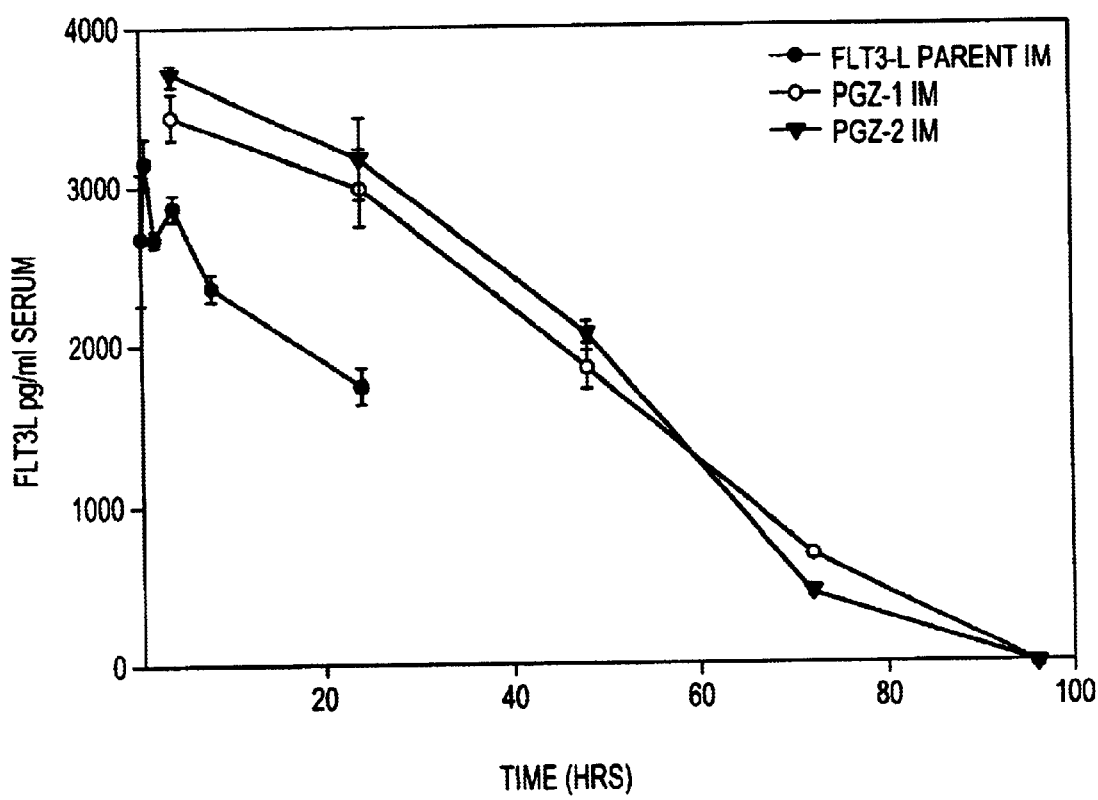
FIG. 4 is a plot in relation to Example 4 of the pharmacokinetic profiles of Flt3-L parent, Flt3-L in PGZ-1, and Flt3-L in PGZ-2. The various formulations (described in Table 2) were injected intramuscularly (i.m.) into Balb/c mice and the levels of Flt3-L in serum were followed for up to 24 hours for the parent formulation or every 24 hours up to 96 hours for the PGZ formulations.
Figure 5A:
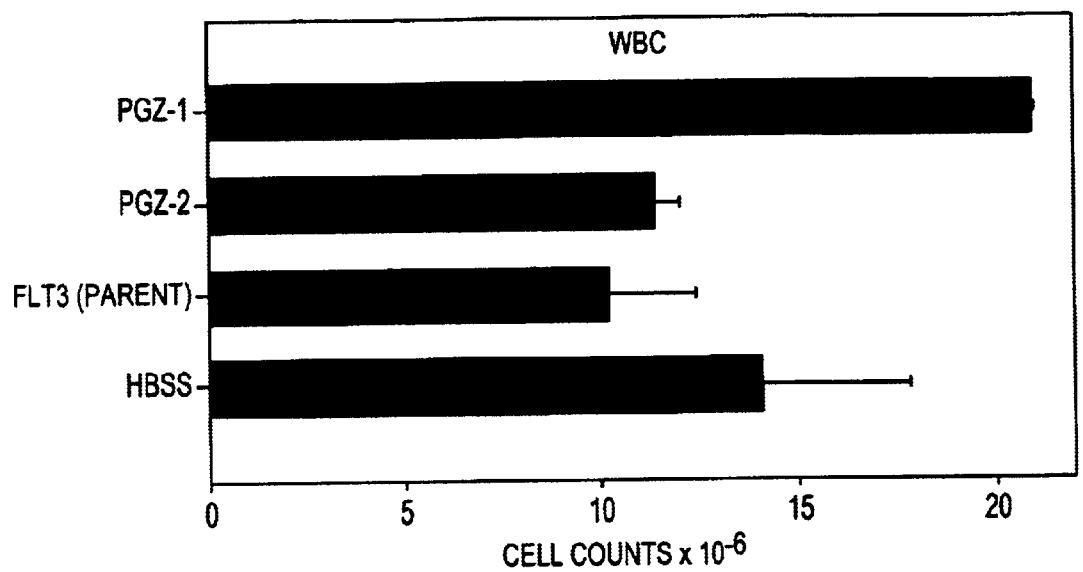
FIG. 5A in relation to Example 4 is a bar chart showing white blood cell counts (WBC) and FIG. 5B is a bar chart showing spleen cell counts (SPC) determined in Balb/c mice following intramuscular (i.m.) injection of Vehicle control, Flt3-L parent, Flt3-L in PGZ-1, or Flt3-L in PGZ-2. Values are Mean+SEM of cell counts determined 96 hours following administration of the various formulations.
Figure 5B:
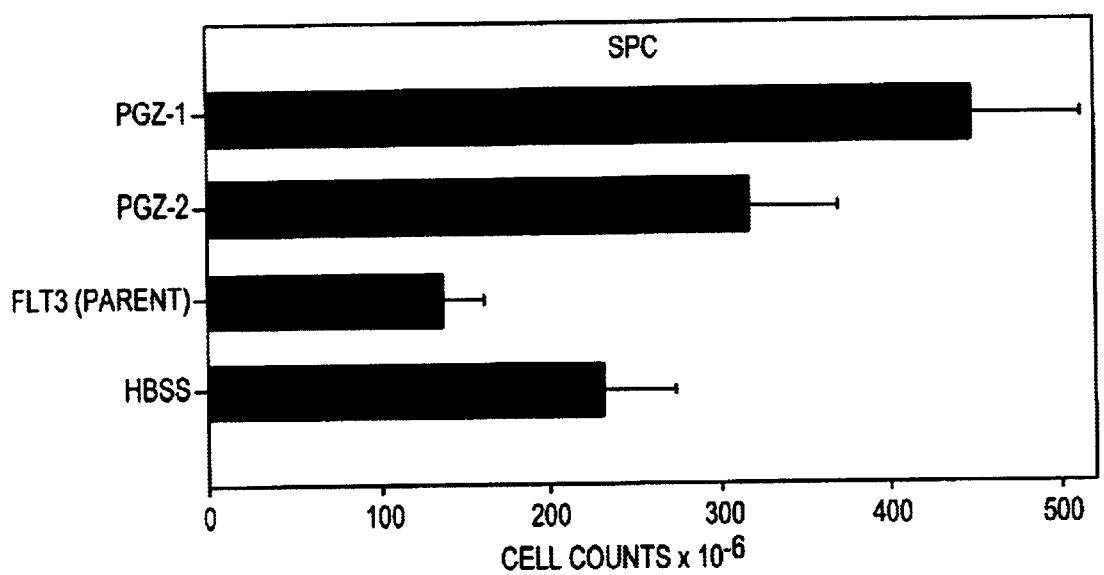

In a study, mice are sacrificed daily up to 4 days after injection and plasma is collected to determine drug pharmacokinetics as well as circulating and splenic white blood cell counts. The pharmacokinetic profile of Flt3-L is shown in FIG. 4. FIGS. 5A and 5B show circulating white blood cells (WBC) and spleen cell counts (SPC). Particularly significant are the much higher white blood cell and spleen cell counts recorded in the case of PGZ-1 vs. PGZ-2, as shown in FIGS. 5A and 5B. This is particularly noteworthy because both formulations exhibit similar pharmacokinetic profiles, as shown in FIG. 4.

To summarize the results in the above-described studies, formulations made according to the present invention:
a) have a longer plasma half-life;
b) increase white cells to a greater extent at equivalent doses compared to conventionally formulated and administered Flt3-L; and
c) increase CFU-GM and HPP-CFC in both the bone marrow and spleen better than conventionally formulated and administered Flt3-L.

The results show a substantial improvement in the delivery of the Flt3-L, using the invention including HPMC being exceptionally good. The improvement can be seen in at least two specific ways, first by providing a more sustained pharmacokinetic profile (longer half-life) and secondly as creating an apparently more potent hematopoietic growth factor than is exhibited by the other formulations. The importance of this can been viewed from a variety of perspectives, including:
a) as a component to a marketed hematopoeitic growth factor, it would likely decrease dose costs of since less growth factor would likely be used to produce the same biological effect;
b) from the patient perspective, if a total lower drug dosage is used, it would be expected to produce fewer side effects (which for hematopoeitic growth factors are often dose limiting, including fever and joint pain); and
C) also from the patient perspective, a better pharmacokinetic profile leads to fewer injections per course of therapy.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for delivering a hematopoietic growth factor capable of expanding, activating, committing or mobilizing hematopoietic stem cells in a host, the method comprising:
   administering a delivery composition to the host, the delivery composition comprising:
   (i) an active agent in a quantity capable of stimulating mobilization in the host of hematopoietic stem cells, the active agent being a hematopoietic growth factor;
   (ii) a first biocompatible polymer and a liquid vehicle in which the first biocompatible polymer is at least partially soluble at some temperature, the first biocompatible polymer being a block copolymer comprising at least one block of a polyoxyalkylene and interacting with the liquid vehicle to impart reverse thermal viscosity behavior to the composition over at least some temperature range, so that the composition is in a lower-viscosity form when the temperature of the composition is at a first temperature within the range and the composition is in a higher-viscosity form when the temperature is at second temperature within the range that is higher than the first temperature; and
   (iii) a second biocompatible polymer being a protective colloid that inhibits dissolution of the first biocompatible polymer into aqueous biological liquids within the host, at least when the delivery composition is in the higher-viscosity form.

2. The method of claim 1, wherein the active agent comprises a cytokine.

3. The method of claim 1, wherein the active agent comprises a plurality of cytokines having additive or synergistic properties for mobilizing the hematopoietic stem cells.

4. The method of claim 1, wherein the active agent comprises a cytokine selected from the group consisting of granulocyte colony-stimulating factor (G-CSF), granulocyte-macrophage colony-stimulating factor (GM-CSF), macrophage colony-stimulating factor (M-CSF), stem cell factor (SCF), interleukin-1 (IL-1), interleukin-2 (IL-2), interleukin-3 (IL-3), interleukin-4 (IL-4), interleukin-6 (IL-6), interleukin-7 (IL-7), interleukin-8 (IL-8), interleukin-11 (IL-11), interleukin-12 (IL-12), Flt3-L, TPO and EPO.

5. The method of claim 1, wherein the active agent is given following the injection of one or more chemotherapeutic drug.

6. The method of claim 5, wherein the chemotherapeutic drug comprises 5-fluorouracil.

7. The method of claim 1, comprising, after the administering, releasing at least a portion of the active agent from the delivery composition, and stimulating CD34+ cell proliferation in the host with the active agent.

8. The method of claim 1, wherein the first temperature is lower than 20° C. and the second temperature is higher than 25° C.

9. The method of claim 8, wherein the first temperature is in a range of from 1° C. to 20° C. and the second temperature is higher than 25 C.

10. The method of claim 9 wherein the second temperature is 37° C.

11. The method of claim 1, wherein the higher-viscosity form has a viscosity that is at least 3 times as large as the viscosity of the lower-viscosity form.

12. The method of claim 1, wherein the lower-viscosity form is a flowable medium and the higher-viscosity form is a gel.

13. The method of claim 1, wherein the second biocompatible polymer has an affinity for water such that the second biocompatible polymer inhibits dissolution of the first biocompatible polymer by aqueous biological fluids within the host.

14. The method of claim 1, wherein the polyoxyalkylene is a polyoxypropylene.

15. The method of claim 1, wherein the polyoxyalkylene is a polyoxyethylene.

16. The method of claim 1, wherein the first biocompatible polymer comprises at least one block of a first polyoxyalkylene and at least one block of a second polyoxyalkylene.

17. The method of claim 16, wherein the first polyoxyalkylene is a polyoxyethylene and the second polyoxyalkylene is a polyoxypropylene.

18. The method of claim 17, wherein the polyoxyethylene comprises at least 70 weight percent of the polymer.

19. The method of claim 17, wherein the polyoxypropylene has the formula $(C_3H_6O)_a$, where a is an integer.

20. The method of claim 17, wherein the polyoxypropylene has the formula

where a is an integer.

21. The method of claim 1, wherein the second biocompatible polymer has a weight average molecular weight of at least 10,000 Daltons.

22. The method of claim 21, wherein the second biocompatible polymer comprises a saccharide-based polymer.

23. The method of claim 21, wherein the second biocompatible polymer comprises cellulosic polymer.

24. The method of claim 23, wherein the cellulosic polymer comprises methylcellulose.

25. The method of claim 23, wherein the cellulosic polymer comprises hydroxymethylcellulose.

26. The method of claim 23, wherein the cellulosic polymer comprises hydroxyethylcellulose.

27. The method of claim 23, wherein the cellulosic polymer comprises hydroxypropyl cellulose.

28. The method of claim 23, wherein the cellulosic polymer comprises hydroxypropyl methylcellulose.

29. The method of claim 23, wherein the cellulosic polymer comprises carboxymethylcellulose.

30. The method of claim 23, wherein the cellulosic polymer comprises ethyl hydroxyethyl cellulose.

31. The method of claim 21, wherein the second biocompatible polymer comprises at least one of carrageenan and a derivative of carrageenan.

32. The method of claim 29, wherein the second biocompatible polymer comprises at least one of algin, alginic acid and an alginate.

33. The method of claim 21, wherein the second biocompatible polymer comprises an alginate.

34. The method of claim 21, wherein the second biocompatible polymer comprises agar.

35. The method of claim 21, wherein the second biocompatible polymer comprises a starch.

36. The method of claim 1, wherein the second biocompatible polymer has a weight average molecular weight of at least 100,000 Daltons.

37. The method of claim 1, wherein the liquid vehicle is an aqueous liquid.

38. The method of claim 1, wherein the liquid vehicle comprises from 60 weight percent to 96 weight percent of the composition, the hematopoietic growth factor comprises from 0.00000001 weight percent to 0.000005 weight percent of the composition, the first biocompatible polymer comprises from 5 weight percent to 33 weight percent of the composition and the second biocompatible polymer comprises from 0.1 weight percent to 5 weight percent of the composition.

39. The method of claim 1, wherein the administering comprises injecting the delivery composition into the host.

40. The method of claim 1, wherein the administering comprises introducing the delivery composition into the host at the first temperature that is lower than the physiologic temperature of the host; and
    the second temperature is at or lower than the physiologic temperature of the host, so that the delivery composition converts from the lower-viscosity form to the higher viscosity form inside the host.

41. The method of claim 40, wherein the lower-viscosity form is a flowable medium and the higher-viscosity form is a gel.

42. The method of claim 41, wherein the delivery composition has a reverse-thermal liquid-gel transition temperature that is higher than the first temperature and that is no higher than the physiologic temperature of the host.

43. The method of claim 1, wherein the host is a mammal.

44. The method of claim 1, wherein the host is a human.

45. The method of claim 1, comprising after the administering, collecting hematopoietic stem cells from the host and later returning at least a portion of the hematopoietic stem cells to the host.

46. The method of claim 45, comprising after the collecting and prior to the returning, enriching the hematopoietic stem cells; and the returning comprises returning to the host at least a portion of the hematopoietic stem cells.

47. The method of claim 46, wherein the enriching comprises immunoadsorption using an antibody for at least a portion of the hematopoietic stem cells.

48. The method of claim 45, comprising after the collecting and prior to the returning, administering at least one treatment selected from the group consisting of chemotherapy and radiotherapy for the treatment of cancer.

49. The method of claim 45, wherein the collecting comprises collecting the hematopoietic stem cells by leukapheresis.

50. The method of claim 45, wherein the collecting comprises collecting peripheral blood containing the hematopoietic stem cells.

51. The method of claim 1, comprising prior to the administering performing a bone marrow transplant on the host.

52. The method of claim 51, wherein the active agent comprises IL-7.

53. The method of claim 1, wherein the hematopoietic stem cells comprise CD34+ cells.

54. The method of any one of claims 1–4 and 6 wherein the administering follows bone marrow transplantation in an amount that improves engraftment.

55. The method of any one of claims 1–4 and 6 wherein the administering comprises administering the delivery composition to the host daily for a plurality of days.

56. The method of any one of claims 1–4 and 6 wherein the host had prior to the administering undergone a peripheral blood leukocyte transplant from a human donor, and the delivery composition, after the administering, improves engraftment of the peripheral blood leukocyte transplant.

57. The method of any one of claims 1–4 and 6 wherein prior to the administering, the host has a hematopoietic disorder.

58. The method of claim 57, wherein the hematopoietic disorder is a result of a viral infection, bacterial infection or fungal infection.

59. The method according to claim 57 wherein the hematopoietic disorder is a result of cancer radiation therapy, chemotherapy or a bone marrow suppressive drug.

60. The method of claim 57, wherein the hematopoietic disorder comprises a side effect of cancer chemotherapy or radiation therapy.

61. The method of claim 57, wherein the hematopoietic disorder comprises at least one of neutropenia, anemia, thrombocytopenia, and immune dysfunction.

62. The method of claim 57, wherein the hematopoietic disorder comprises a congenital or neoplastic associated neutropenia.

63. The method of claim 57, wherein the hematopoietic disorder comprises neutropenia associated with therapy for HIV.

64. The method of claim 1, wherein the hematopoietic growth factor is G-CSF.

65. The method of claim 1, wherein the hematopoietic growth factor is GM-CSF.

66. The method of claim 1, wherein the hematopoietic growth factor is Flt3-L.

67. The method of claim 1, wherein the hematopoietic growth factor is M-CSF.

68. The method of claim 1, wherein the hematopoietic growth factor is SCF.

69. The method of claim 1, wherein the hematopoietic growth factor is IL-1.

70. The method of claim 1, wherein the hematopoietic growth factor is IL-2.

71. The method of claim 1, wherein the hematopoietic growth factor is IL-3.

72. The method of claim 1, wherein the hematopoietic growth factor is IL-4.

73. The method of claim 1, wherein the hematopoietic growth factor is IL-6.

74. The method of claim 1, wherein the hematopoietic growth factor is IL-7.

75. The method of claim 1, wherein the hematopoietic growth factor is IL-8.

76. The method of claim 1, wherein the hematopoietic growth factor is IL-11.

77. The method of claim 1, wherein the hematopoietic growth factor is IL-12.

78. The method of claim 1, wherein the hematopoietic growth factor is TPO.

79. The method of claim 1, wherein the hematopoietic growth factor is EPO.

* * * * *

UNITED STATES PATENT AND TRADEMARK OFFICE
CERTIFICATE OF CORRECTION

PATENT NO.    : 6,649,189 B2
DATED         : November 18, 2003
INVENTOR(S)   : Talmadge et al.

It is certified that error appears in the above-identified patent and that said Letters Patent is hereby corrected as shown below:

Column 21,
Line 29, delete "$(OCHCH_2)_b$", and insert therefor -- $(OCHCH_2)_a$ --.

Column 23,
Line 10, delete the word "hematopoletic", and insert therefor -- hematopoietic --.

Signed and Sealed this

Second Day of March, 2004

JON W. DUDAS
*Acting Director of the United States Patent and Trademark Office*